US011548788B2

United States Patent
Cornelius et al.

(10) Patent No.: US 11,548,788 B2
(45) Date of Patent: Jan. 10, 2023

(54) SPHERICAL SILICA FOR TUBULE OCCLUSION

(71) Applicant: Evonik Operations GmbH, Essen (DE)

(72) Inventors: John M. Cornelius, Forest Hills, MD (US); William J. Hagar, Perryville, MD (US); Karl W. Gallis, Perryville, MD (US); Terry W. Nassivera, Gambrills, MD (US)

(73) Assignee: Evonik Operations GmbH, Essen (DE)

( * ) Notice: Subject to any disclaimer, the term of this patent is extended or adjusted under 35 U.S.C. 154(b) by 158 days.

(21) Appl. No.: 16/642,240

(22) PCT Filed: Aug. 24, 2018

(86) PCT No.: PCT/EP2018/072875
§ 371 (c)(1),
(2) Date: Feb. 26, 2020

(87) PCT Pub. No.: WO2019/042887
PCT Pub. Date: Mar. 7, 2019

(65) Prior Publication Data
US 2021/0024359 A1 Jan. 28, 2021

Related U.S. Application Data

(60) Provisional application No. 62/550,725, filed on Aug. 28, 2017.

(51) Int. Cl.
*C01B 33/193* (2006.01)
*A61K 8/02* (2006.01)
(Continued)

(52) U.S. Cl.
CPC ............ *C01B 33/193* (2013.01); *A61K 8/025* (2013.01); *A61K 8/25* (2013.01); *A61Q 11/00* (2013.01);
(Continued)

(58) Field of Classification Search
CPC ........ C01B 33/193; A61K 8/025; A61K 8/25; A61Q 11/00
See application file for complete search history.

(56) References Cited

U.S. PATENT DOCUMENTS 6,946,119 B2    9/2005  Gallis et al.
7,255,852 B2    8/2007  Gallis et al.
(Continued)

FOREIGN PATENT DOCUMENTS

JP    63-182212 A    7/1988
JP    2013-544883 A   12/2013
(Continued)

OTHER PUBLICATIONS

International Search Report and Written Opinion dated Nov. 28, 2018 in PCT/EP2018/072875 filed Aug. 24, 2018.
(Continued)

*Primary Examiner* — James A Fiorito
(74) *Attorney, Agent, or Firm* — Oblon, McClelland, Maier & Neustadt, L.L.P.

(57) ABSTRACT

Spherical silica and/or silicate particles having a d50 median particle size from 1 to 5 μm, a d95 particle size less than 8 μm, an oil absorption from 40 to 100 cc/100 g, a pack density from 20 to 60 lb/ft³, and a sphericity factor ($S_{80}$) of at least 0.9, are disclosed, as well as methods for making these spherical particles, and dentifrice compositions containing the spherical particles.

26 Claims, 8 Drawing Sheets

(51) Int. Cl.
   *A61K 8/25*   (2006.01)
   *A61Q 11/00*  (2006.01)
(52) U.S. Cl.
   CPC .... *A61K 2800/28* (2013.01); *A61K 2800/412* (2013.01); *C01P 2004/32* (2013.01); *C01P 2004/61* (2013.01); *C01P 2006/12* (2013.01); *C01P 2006/19* (2013.01)

(56) References Cited

U.S. PATENT DOCUMENTS

| | | | |
|---|---|---|---|
| 7,438,895 B2 | 10/2008 | Gallis et al. | |
| 8,609,068 B2 | 12/2013 | Hagar et al. | |
| 8,945,517 B2 | 2/2015 | Hagar et al. | |
| 9,028,605 B2 | 5/2015 | Hagar et al. | |
| 9,186,307 B2 | 11/2015 | Gallis et al. | |
| 9,327,988 B2 | 5/2016 | Hagar et al. | |
| 9,617,162 B2 | 4/2017 | Hagar et al. | |
| 10,287,438 B2 | 5/2019 | Nassivera et al. | |
| 10,328,002 B2 | 6/2019 | Dolan et al. | |
| 2007/0003465 A1* | 1/2007 | Huang | A61K 8/25 423/335 |
| 2011/0206746 A1 | 8/2011 | Hagar et al. | |
| 2013/0251772 A1 | 9/2013 | Chopra et al. | |
| 2014/0072634 A1 | 3/2014 | Hagar et al. | |
| 2015/0086463 A1 | 3/2015 | Hagar et al. | |
| 2016/0214865 A1 | 7/2016 | Hagar et al. | |
| 2016/0326373 A1 | 11/2016 | Nassivera et al. | |
| 2017/0087066 A1 | 3/2017 | Nassivera et al. | |
| 2018/0168958 A1 | 6/2018 | Dolan et al. | |

FOREIGN PATENT DOCUMENTS

| | | |
|---|---|---|
| WO | WO 2018/114280 A1 | 6/2018 |
| WO | WO 2018/118382 A1 | 6/2018 |

OTHER PUBLICATIONS

Chemical and Engineering News, vol. 63, No. 5, Feb. 4, 1985, p. 27.

Stephen Brunauer, et al., "Adsorption of Gases in Multimolecular Layers," J. Am. Chem. Soc., vol. 60, Feb. 1938, pp. 309-319.

U.S. Appl. No. 11/646,125, filed Dec. 27, 2006, US 2008-0160053 A1, McGill, et al.

U.S. Appl. No. 14/920,951, filed Oct. 23, 2015, US 2016-0038387 A1, Gallis, et al.

U.S. Appl. No. 14/204,660, filed Mar. 11, 2014, US 2014-0272012 A1, Gallis, et al.

U.S. Appl. No. 15/275,541, filed Sep. 26, 2016, US 2017-0087066 A1, Nassivera, et al.

U.S. Appl. No. 16/470,467, filed Jun. 17, 2019, Gallis, et al.

* cited by examiner

Electron Image 1

SPHERICAL SILICA FOR TUBULE OCCLUSION

BACKGROUND OF THE INVENTION

Tooth sensitivity is a common problem with many people and is increasingly prevalent in the ageing population. The condition occurs as the protective layer of enamel over the teeth and/or the gums recedes and exposes the dentin layer. The dentin is a much less mineralized material that is comprised of both mineral (hydroxyl apatite) and organic content (collagen). The dentin layer is also porous, with round tubules that extend from the root of the tooth outward and allow for the transfer of nutrients to different parts of the tooth. When these tubules are exposed to external stimuli, such as heat, cold or polysaccharides, it is postulated that the fluid in the tubules changes in pressure (due to expansion/contraction) and causes the pain associated with sensitive teeth. Potassium nitrate is commonly added to sensitive toothpaste formulations to act as a nerve blocking agent, where the potassium ions interfere with the ability of the tooth to send pain signals to the brain. The conditions responsible for the pain are still present; however, the pain is no longer felt after a sufficient concentration of potassium ions is built up in the region. Since it is recommended the potassium nitrate toothpastes are not used for a period of more than two continuous weeks, other sensitivity reduction agents are typically used alone or in conjunction with potassium nitrate. Remineralizing agents, which foster the formation of new hydroxyl apatite through the precipitation of soluble calcium and phosphate ions that repair the enamel surface, can be used (e.g., Novamin-bioglass type materials). These materials introduce a unique set a formulating challenges since the ingredients typically need to remain separate before application (dual tube or hydrophobic formulation), and they are typically not compatible with sodium fluoride (Ca ions).

Tubule occlusion techniques, in which a physical blocking of the tubule with a particle takes place, also can be used. Certain silica particles can occlude tubules, and their affinity toward hydroxyapatite can be modified with the addition of an adduct material. Typically, the silica particles have to be air milled to achieve the proper particle size distribution that is required to fit into a tubule (e.g., 2-3 µm). The addition of these silica materials can be used for tubule occlusion, but such materials provide substantial viscosity build—functioning as a thickening silica—and do not provide significant cleaning. Lower structure silicas can be used, but problems with the milling, such as lower brightness levels and trace metal contamination (from milling) can result in unacceptable attributes. The abrasive nature of these materials toward enamel (measured by REA) can tend to remove amorphous hydroxyapatite as new enamel is forming.

Therefore, it would be beneficial to provide silica materials with improved tubule occlusion performance, but still maintain cleaning performance in a dentifrice composition. Accordingly, it is to these ends that the present invention is principally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Silica and/or silicate particles that can be used for tubule occlusion are disclosed and described herein. In accordance with an aspect of this invention, such silica and/or silicate particles can have (i) a d50 median particle size in a range from about 1 to about 5 µm, (ii) a d95 particle size of less than or equal to about 8 µm, (iii) an oil absorption in a range from about 40 to about 100 cc/100 g, (iv) a pack density in a range from about 20 to about 60 lb/ft$^3$, and (v) a sphericity factor ($S_{80}$) of greater than or equal to about 0.9. These silica and/or silicate particles have a spherical shape or morphology, and can be produced using a continuous loop reactor process.

Also disclosed herein are dentifrice compositions containing the spherical silica and/or silicate particles, typically at amounts in the 0.5-50 wt. % range, and methods of using the silica and/or silicate particles and compositions.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

Figure 1:
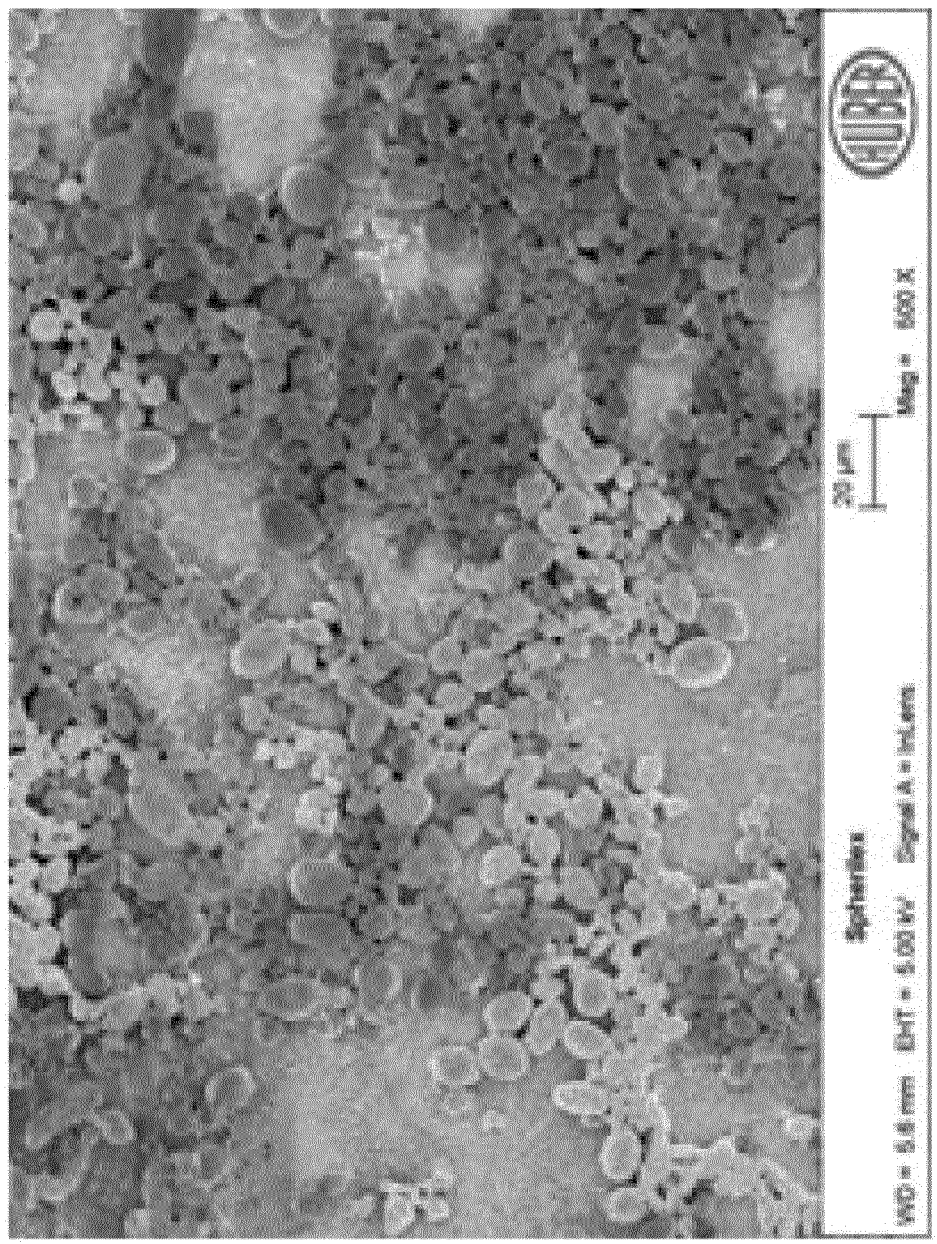
FIG. 1 is a Scanning Electron Micrograph of the silica of Example 2A.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated and can be interchanged, with or without explicit description of the particular combination. Accordingly, unless explicitly recited otherwise, any aspect or feature disclosed herein can be combined to describe inventive designs, compositions, processes, or methods consistent with the present disclosure.

While compositions and methods are described herein in terms of "comprising" various components or steps, the compositions and methods can also "consist essentially of" or "consist of" the various components or steps, unless stated otherwise.

The terms "a," "an," and "the" are intended to include plural alternatives, e.g., at least one, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, and so forth.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. As a representative example, the BET surface area of the silica and/or silicate particles can be in certain ranges in various aspects of this invention. By a disclosure that the BET surface area is in a range from about 25 to about 100 $m^2/g$, the intent is to recite that the surface area can be any surface area within the range and, for example, can be equal to about 25, about 30, about 40, about 50, about 60, about 70, about 80, about 90, or about 100 $m^2/g$. Additionally, the surface area can be within any range from about 25 to about 100 $m^2/g$ (for example, from about 45 to about 90 $m^2/g$), and this also includes any combination of ranges between about 25 and about 100 $m^2/g$ (for example, the surface area can be in a range from about 25 to about 50 $m^2/g$ or from about 70 to about 90 $m^2/g$). Likewise, all other ranges disclosed herein should be interpreted in a manner similar to this example.

DETAILED DESCRIPTION OF THE INVENTION

Disclosed herein are generally spherical silica and/or silicate particles that can be characterized by (i) a d50 median particle size in a range from about 1 to about 5 μm, (ii) a d95 particle size of less than or equal to about 8 μm, (iii) an oil absorption in a range from about 40 to about 100 cc/100 g, (iv) a pack density in a range from about 20 to about 60 lb/ft$^3$, and (v) a sphericity factor ($S_{80}$) of greater than or equal to about 0.9.

Methods of making these spherical silica and/or silicate particles, dentifrice compositions containing the spherical particles, and methods of treatment using the spherical particles and dentifrice compositions also are disclosed and described herein.

Spherical Silica/Silicate Particles

Consistent with aspects of the present invention, spherical silica and/or silicate particles with improved tubule occlusion can have the following characteristics: (i) a d50 median particle size in a range from about 1 to about 5 μm, (ii) a d95 particle size of less than or equal to about 8 μm, (iii) an oil absorption in a range from about 40 to about 100 cc/100 g, (iv) a pack density in a range from about 20 to about 60 lb/ft$^3$, and (v) a sphericity factor ($S_{80}$) of greater than or equal to about 0.9. In further aspects, such silica and/or silicate particles consistent with the present invention also can have any of the characteristics or properties provided below, and in any combination.

In an aspect, the spherical silica and/or silicate particles can have a relatively small average particle size. Often, the median particle size (d50) and/or mean particle size (average) can fall within a range from about from about 1 to about 5, from about 1 to about 4.5, from about 1 to about 4, from about 1.5 to about 5, from about 1.5 to about 4.5, or from about 1.5 to about 4 μm, and the like. In some aspects, the median particle size (d50) and/or mean particle size (average) can fall within a range from about 2 to about 5, from about 2 to about 4.5, from about 2 to about 4, or from about 2.5 to about 3.8 μm. Other appropriate ranges for the mean and median particle sizes are readily apparent from this disclosure.

In an aspect, the spherical silica and/or silicate particles can have a narrow particle size distribution, as reflected by the d95 particle size. Often, the d95 particle size can be less than or equal to about 8 μm, less than or equal to about 7.5 μm, less than or equal to about 7 μm, less than or equal to about 6.5 μm, less than or equal to about 6 μm, or less than or equal to about 5.5 μm. The narrow particle size distribution also can be reflected in the weight percent of 325 mesh residue (amount retained in a 325 mesh sieve), which generally can be less than or equal to about 0.9 wt. %. In some aspects, the 325 mesh residue can be less than or equal to about 0.7 wt. %, less than or equal to about 0.5 wt. %, less than or equal to about 0.3 wt. %, less than or equal to about 0.2 wt. %, or less than or equal to about 0.1 wt. %. Other appropriate ranges for the d95 particle size and the 325 mesh residue are readily apparent from this disclosure.

Generally, the silica and/or silicate particles can have a relatively low oil absorption, typically in a range from about 40 to about 100 cc/100 g, or from about 45 to about 90 cc/100 g, in some aspects of this invention. In other aspects, the oil absorption can range from about 50 to about 85 cc/100 g, or from about 60 to about 80 cc/100 g. Other appropriate ranges for the oil absorption are readily apparent from this disclosure.

While not being limited thereto, the spherical silica and/or silicate particles can have a pack density in a range from about 20 to about 60 lb/ft$^3$ in one aspect of the invention. In another aspect, the pack density can be in a range from about 25 to about 55 lb/ft$^3$, from about 25 to about 50 lb/ft$^3$, or from about 30 to about 50 lb/ft$^3$. In yet another aspect, the pack density can be in the range from about 35 to about 45 lb/ft$^3$. Other appropriate ranges for the pack density are readily apparent from this disclosure.

The sphericity of the spherical silica and/or silicate particles can be quantified by a sphericity factor ($S_{80}$), which is typically greater than or equal to about 0.85, greater than or equal to about 0.88, or greater than or equal to about 0.9. The sphericity factor ($S_{80}$) is determined as follows. An SEM image of the silica and/or silicate particle sample is magnified 20,000 times, which is representative of the silica and/or silicate particle sample, and is imported into photo imaging software, and the outline of each particle (two-dimensionally) is traced. Particles that are close in proximity to one another but not attached to one another should be considered separate particles for this analysis. The outlined particles are then filled in with color, and the image is imported into particle characterization software (e.g., IMAGE-PRO PLUS available from Media Cybernetics, Inc., Bethesda, Md.) capable of determining the perimeter and area of the particles. Sphericity of the particles can then be calculated according to the equation, Sphericity=(perimeter) divided by ($4\pi \times$area), wherein perimeter is the software measured perimeter derived from the outlined trace of the particles, and wherein area is the software measured area within the traced perimeter of the particles.

The sphericity calculation is performed for each particle that fits entirely within the SEM image. These values are then sorted by value, and the lowest 20% of these values are discarded. The remaining 80% of these values are averaged to obtain the sphericity factor ($S_{80}$). Additional information on sphericity can be found in U.S. Pat. Nos. 8,945,517 and 8,609,068, incorporated herein by reference in their entirety.

In one aspect of this invention, the spherical silica and/or silicate particles can have a sphericity factor ($S_{80}$) greater than or equal to about 0.85, or greater than or equal to about 0.88, while in another aspect, the sphericity factor ($S_{80}$) can be greater than or equal to about 0.9. Yet, in another aspect, the spherical silica and/or silicate particles can be characterized by a sphericity factor ($S_{80}$) greater than or equal to about 0.92, and in still another aspect, the silica and/or silicate particles can be characterized by a sphericity factor ($S_{80}$) greater than or equal to about 0.94. As one of skill in the art would readily recognize, a 3-dimensional sphere (or 2-dimensional circle) will have a sphericity factor ($S_{80}$) equal to 1.

The spherical silica and/or silicate particles can have any suitable surface area, generally a BET surface area ranging from about 25 to about 100 m$^2$/g. Often, the BET surface area can fall within a range from about 35 to about 95, from about 40 to about 90, or from about 45 to about 95 m$^2$/g. In further aspects, the BET surface area can be in a range from about 20 to about 100, from about 20 to about 80, from about 50 to about 100, from about 60 to about 100, from about 40 to about 85, from about 50 to about 80, or from about 55 to about 80 m$^2$/g, and the like. Other appropriate ranges for the BET surface area are readily apparent from this disclosure.

Additionally, the spherical silica and/or silicate particles can be less abrasive, as reflected by an Einlehner abrasion value ranging from about 1 to about 15 mg lost/100,000 revolutions. For instance, the Einlehner abrasion value can be in a range from about 1 to about 10; alternatively, from about 2 to about 12; or alternatively, from about 2 to about 7 mg lost/100,000 revolutions. Other appropriate ranges for the Einlehner abrasion value are readily apparent from this disclosure.

In another aspect, the spherical silica and/or silicate particles can have relatively low water absorption. For instance, the water absorption can be in a range from about 55 to about 115 cc/100 g, from about 70 to about 100 cc/100 g, or from about 65 to about 90 cc/100 g. Other appropriate ranges for the water absorption are readily apparent from this disclosure.

In these and other aspects, any of the spherical silica and/or silicate particles can be amorphous, can be synthetic, or can be both amorphous and synthetic. Moreover, the spherical silica and/or silicate particles can comprise precipitated silica and/or silicate particles in particular aspects of this invention, although not limited thereto.

In one aspect of this invention, the spherical silica and/or silicate particles can comprise silica particles, while in another aspect, the spherical silica and/or silicate particles can comprise silicate particles, and in yet another aspect, the spherical silica and/or silicate particles can comprise both silica and silicate particles (e.g., a mixture of silica and silicate particles). When the spherical particles contain silicate particles, any suitable silicate material can be used, non-limiting examples of which can include calcium silicate particles, magnesium silicate particles, sodium aluminosilicate particles (or other alkali metal aluminosilicates), sodium magnesium aluminosilicate particles (or other alkaline earth metal-modified alkali metal aluminosilicates), and the like, as well as combinations thereof.

Processes for Producing Spherical Particles

The spherical silica and/or silicate particles disclosed herein are not limited to any particular synthesis procedure. However, in order to achieve the desired sphericity, a continuous loop reactor process can be utilized to form the spherical silica and/or silicate particles. This process and associated reactor system (which can include a continuous loop of one or more loop reactor pipes) are described in U.S. Pat. Nos. 8,945,517 and 8,609,068, incorporated herein by reference in their entirety. In general, the continuous loop process involves (a) continuously feeding a mineral acid and an alkali metal silicate into a loop reaction zone comprising a stream of liquid medium, wherein at least a portion of the mineral acid and the alkali metal silicate react to form a silica product (e.g., the silica and/or silicate particles) in the liquid medium of the loop reaction zone; (b) continuously recirculating the liquid medium through the loop reaction zone; and (c) continuously discharging from the loop reaction zone a portion of the liquid medium comprising the silica product. Typically, the feed locations of the mineral acid and the alkali metal silicate into the loop reaction zone are different, and the total feed rate of acid and silicate is proportional to, and often equal to, the discharge rate of the liquid medium containing the silica product. All or substantially of the contents within the loop reaction zone are recirculated, for instance, at a rate ranging from about 50 vol. % per minute (the recirculation rate, per minute, is one-half of the total volume of the contents) to about 1000 vol. % per minute (the recirculation rate, per minute, is ten times the total volume of the contents), or from about 75 vol. % per minute to about 500 vol. % per minute.

Dentirfrice Compositions

The spherical silica and/or silicate particles can be used in any suitable composition and for any suitable end-use application. Often, the silica and/or silicate particles can be used in oral care applications, such as in a dentifrice composition. The dentifrice composition can contain any suitable amount of the silica and/or silicate particles, such as from about 0.5 to about 50 wt. %, from about 1 to about 50 wt. %, from about 5 to about 35 wt. %, from about 10 to about 40 wt. %, or from about 10 to about 30 wt. %, of the spherical silica and/or silicate particles. These weight percentages are based on the total weight of the dentifrice composition.

The dentifrice composition can be in any suitable form, such as a liquid, powder, or paste. In addition to the silica and/or silicate particles, the dentifrice composition can contain other ingredients or additives, non-limiting examples of which can include a humectant, a solvent, a binder, a therapeutic agent, a chelating agent, a thickener other than the silica and/or silicate particles, a surfactant, an abrasive other than the silica and/or silicate particles, a sweetening agent, a colorant, a flavoring agent, a preservative, and the like, as well as any combination thereof.

Humectants serve to add body or "mouth texture" to a dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, and mixtures thereof. In some formulations, humectants are present in an amount from about 20 to about 50 wt. %, based on the weight of dentifrice composition.

A solvent can be present in the dentifrice composition, at any suitable loading, and usually the solvent comprises water. When used, water is preferably deionized and free of impurities, can be present in the dentifrice at loadings from 5 to about 70 wt. %, or from about 5 to about 35 wt. %, based on the weight of dentifrice composition.

Therapeutic agents also can be used in the compositions of this invention to provide for the prevention and treatment of dental caries, periodontal disease, and temperature sensitivity, for example. Suitable therapeutic agents can include, but are not limited to, fluoride sources, such as sodium fluoride, sodium monofluorophosphate, potassium mono fluorophosphate, stannous fluoride, potassium fluoride, sodium fluorosilicate, ammonium fluorosilicate and the like; condensed phosphates such as tetrasodium pyrophosphate, tetrapotassium pyrophosphate, disodium dihydrogen pyrophosphate, trisodium monohydrogen pyrophosphate; tripolyphosphates, hexametaphosphates, trimetaphosphates and pyrophosphates; antimicrobial agents such as triclosan, bisguanides, such as alexidine, chlorhexidine and chlorhexidine gluconate; enzymes such as papain, bromelain, glucoamylase, amylase, dextranase, mutanase, lipases, pectinase, tannase, and proteases; quaternary ammonium compounds, such as benzalkonium chloride (BZK), benzethonium chloride (BZT), cetylpyridinium chloride (CPC), and domiphen bromide; metal salts, such as zinc citrate, zinc chloride, and stannous fluoride; sanguinaria extract and sanguinarine; volatile oils, such as eucalyptol, menthol, thymol, and methyl salicylate; amine fluorides; peroxides and the like. Therapeutic agents can be used in dentifrice formulations singly or in combination, and at any therapeutically safe and effective level or dosage.

Thickening agents are useful in the dentifrice compositions to provide a gelatinous structure that stabilizes the toothpaste against phase separation. Suitable thickening agents include silica thickener; starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof. Typical levels of thickening agents or binders are up to about 15 wt. % of a toothpaste or dentifrice composition.

Useful silica thickeners for utilization within a toothpaste composition, for example, include, as a non-limiting example, an amorphous precipitated silica such as ZEODENT 165 silica. Other non-limiting silica thickeners include ZEODENT 153, 163 and/or 167 and ZEOFREE 177 and/or 265 silica products, all available from J. M. Huber Corporation.

Surfactants can be used in the dentifrice compositions of the invention to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants such as sodium lauryl sulfate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine and the like. Sodium lauryl sulfate is a preferred surfactant. The surfactant is typically present in the compositions of the present invention in an amount from about 0.1 to about 15 wt. %, from about 0.3 to about 5 wt. %, or from about 0.3 to about 2.5 wt. %.

The disclosed silica and/or silicate particles can be utilized alone as the abrasive in the dentifrice composition, or as an additive or co-abrasive with other abrasive materials discussed herein or known in the art. Thus, any number of other conventional types of abrasive additives can be present within the dentifrice compositions of the invention. Other such abrasive particles include, for example, precipitated calcium carbonate (PCC), ground calcium carbonate (GCC), chalk, bentonite, dicalcium phosphate or its dihydrate forms, silica gel (by itself, and of any structure), precipitated silica, amorphous precipitated silica (by itself, and of any structure as well), perlite, titanium dioxide, dicalcium phosphate, calcium pyrophosphate, alumina, hydrated alumina, calcined alumina, aluminum silicate, insoluble sodium metaphosphate, insoluble potassium metaphosphate, insoluble magnesium carbonate, zirconium silicate, particulate thermosetting resins and other suitable abrasive materials. Such materials can be introduced into the dentifrice compositions to tailor the polishing characteristics of the target formulation.

Sweeteners can be added to the dentifrice composition (e.g., toothpaste) to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, mannose, and glucose.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Flavoring agents also can be added to dentifrice compositions. Suitable flavoring agents include, but are not limited to, oil of wintergreen, oil of peppermint, oil of spearmint, oil of sassafras, and oil of clove, cinnamon, anethole, menthol, thymol, eugenol, eucalyptol, lemon, orange and other such flavor compounds to add fruit notes, spice notes, etc. These flavoring agents generally comprise mixtures of aldehydes, ketones, esters, phenols, acids, and aliphatic, aromatic and other alcohols.

Preservatives also can be added to the compositions of the present invention to prevent bacterial growth. Suitable preservatives approved for use in oral compositions such as methylparaben, propylparaben and sodium benzoate can be added in safe and effective amounts.

Other ingredients can be used in the dentifrice composition, such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like.

Methods of Use

Any of the spherical silica and/or silicate particles and any of the compositions disclosed herein can be used in methods of treatment. For instance, a method of reducing dental sensitivity consistent with this invention can comprise contacting any of the spherical silica and/or silicate particles (or any of the compositions) disclosed herein with a surface of a mammalian tooth. Thus, the silica and/or silicate particles (or compositions) can be applied to, or delivered to, the surface of the mammalian tooth via brushing or any other suitable technique. Any suitable amount of the silica and/or silicate particles (or compositions) can be used, and for any appropriate period of time.

In another aspect, a method for occluding a dentin tubule within a surface of a mammalian tooth consistent with this invention can comprise contacting any of the spherical silica and/or silicate particles (or any of the compositions) disclosed herein with the surface of the mammalian tooth. As above, any suitable amount of the silica and/or silicate particles (or compositions) can be applied to, or delivered to, the surface of the mammalian tooth via brushing or any other suitable technique, and for any appropriate period of time.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

The BET surface areas disclosed herein were determined on a Micromeritics TriStar II 3020 V1.03 using the BET nitrogen adsorption method of Brunaur et al., J. Am. Chem. Soc., 60, 309 (1938), and such technique is well known to those skilled in the art.

CTAB surface areas disclosed herein were determined by absorption of CTAB (cetyltrimethylammonium bromide) on the silica surface, the excess separated by centrifugation and the quantity determined by titration with sodium lauryl sulfate using a surfactant electrode. Specifically, about 0.5 grams of the silica and/or silicate particles were placed in a 250-mL beaker with 100 mL CTAB solution (5.5 g/L), mixed on an electric stir plate for 1 hour, then centrifuged for 30 min at 10,000 RPM. One mL of 10% Triton X-100 was added to 5 mL of the clear supernatant in a 100-mL beaker. The pH was adjusted to 3-3.5 with 0.1 N HCl and the specimen was titrated with 0.01 M sodium lauryl sulfate using a surfactant electrode (Brinkmann SUR1501-DL) to determine the endpoint.

The median particle size (d50) refers to the particle size for which 50% of the sample has a smaller size and 50% of the sample has a larger size. Median particle size (d50), mean particle size (average), and d95 were determined via the laser diffraction method using a Horiba LA 300 instrument. Dry particles were submitted to the instrument for analysis.

For pour density and pack density, 20 grams of the sample were placed into a 250 mL graduated cylinder with a flat rubber bottom. The initial volume was recorded and used to calculate the pour density by dividing it into the weight of sample used. The cylinder was then placed onto a tap density machine where it was rotated on a cam at 60 RPM. The cam is designed to raise and drop the cylinder a distance of 5.715 cm once per second, until the sample volume is constant, typically for 15 min. This final volume is recorded and used to calculate the packed density by dividing it into the weight of sample used.

The Einlehner abrasion value is a measure of the hardness/abrasiveness of silica and/or silicate particles, and is described in detail in U.S. Pat. No. 6,616,916, incorporated herein by reference, and involves an Einlehner AT-1000 Abrader generally used as follows: (1) a Fourdrinier brass wire screen is weighed and exposed to the action of a 10% aqueous silica suspension for a fixed length of time; (2) the amount of abrasion is then determined as milligrams of brass lost from the Fourdrinier wire screen per 100,000 revolutions (mg lost/100,000 revolutions).

Oil absorption values were determined in accordance with the rub-out method described in ASTM D281 using linseed oil (cc oil absorbed per 100 g of the particles). Generally, a higher oil absorption level indicates a particle with a higher level of large pore porosity, also described as higher structure.

Water absorption values were determined with an Absorptometer "C" torque rheometer from C. W. Brabender Instruments, Inc. Approximately ⅓ of a cup of the silica sample was transferred to the mixing chamber of the Absorptometer and mixed at 150 RPM. Water then was added at a rate of 6 mL/min, and the torque required to mix the powder was recorded. As water is absorbed by the powder, the torque will reach a maximum as the powder transforms from free-flowing to a paste. The total volume of water added when the maximum torque was reached was then standardized to the quantity of water that can be absorbed by 100 g of powder. Since the powder was used on an as received basis (not previously dried), the free moisture value of the powder was used to calculate a "moisture corrected water AbC value" by the following equation.

$$\text{Water Absorption} = \frac{\text{water absorbed } (cc) + \% \text{ moisture}}{(100 \text{ (g)} - \% \text{ moisture})/100}$$

The Absorptometer is commonly used to determine the oil number of carbon black in compliance with ASTM D 2414 methods B and C and ASTM D 3493.

The pH values disclosed herein (5% pH) were determined in an aqueous system containing 5 wt. % solids in deionized water using a pH meter.

The 325 mesh residue (wt. %) of the silica sample was measured utilizing a U.S. Standard Sieve No. 325, with 44 micron or 0.0017 inch openings (stainless steel wire cloth), by weighing a 10.0 gram sample to the nearest 0.1 gram into the cup of a 1 quart Hamilton mixer (Model No. 30), adding approximately 170 mL of distilled or deionized water, and stirring the slurry for at least 7 min. The mixture was transferred onto the 325 mesh screen and water was sprayed directly onto the screen at a pressure of 20 psig for two minutes, with the spray head held about four to six inches from the screen. The remaining residue was then transferred to a watch glass, dried in an oven at 150° C. for 15 min, then cooled, and weighed on an analytical balance.

Example 1A

Irregular Silica Particles

Table I summarize certain properties of comparative silica material 1A, which has an irregular and non-spherical particle morphology. Example 1A was a conventional silica material commercially available from Huber Engineered Materials.

Example 2A

Spherical Silica Particles

A continuous loop reactor process (see e.g., U.S. Pat. Nos. 8,945,517 and 8,609,068) was used to produce the silica particles of Example 2A, which have a spherical morphology and a tighter particle size distribution (e.g., less 325 mesh residue in the final silica product). No milling step was used.

For Example 2A, 1.5 kg of precipitated silica, 1.34 kg of sodium sulfate, 11.1 L of sodium silicate (3.32 MR, 13.3%) and 20 L of water were added to the recirculation loop, followed by heating to 83° C. with recirculation at 80 L/min with the Silverson operating at 60 Hz (3485 RPM). Sodium silicate (3.32 MR, 13.3%) and sulfuric acid (11.4%) were added simultaneously to the loop at a silicate rate of 2.1 L/min and an acid rate sufficient to maintain a pH of 7.5. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected, addition of acid and silicate were stopped and the contents of the loop were allowed to circulate. The silica product in the collection vessel was adjusted to pH 6.0 with the manual addition of sulfuric acid and was then filtered, and washed to a conductivity of ~1500 µS. The pH of the slurry was then readjusted to pH 6.0 with sulfuric acid and spray dried.

Table I summarizes certain properties of the silica particles produced in Example 2A, as compared to the respective properties of Example 1A. Example 2A had a d50 median particle size of 3.1 µm, a d95 particle size of 6.0 µm, an oil absorption of 68 cc/100 g, and a pack density of 40 lb/ft$^3$. Representative FIG. 1 is an SEM image that demonstrates the narrow particle size distribution and spherical particle morphology of Example 2A. The sphericity factor ($S_{80}$) for Example 2A was greater than 0.9.

Example 1B-2B

Toothpaste Formulations and Tubule Occlusion Testing

Samples of silicas 1A-2A were used in toothpaste formulations 1B-2B as summarized in Table II. Since the pour density of the 3.1 µm spherical silica of Example 2A was about 6 times that of Example 1A, additional spherical silica was added to formulation 2B to keep the number of silica particles in the formulation approximately the same (5 wt. % of 3.1 µm spherical silica in Example 2B versus 0.8 wt. % of the Example 1A silica in Example 1B).

For tubule occlusion testing, bovine incisors were obtained from a local slaughter house. The teeth were rinsed in water and sterilized in an autoclave, then rinsed in water to remove any remaining tissue, and stored in isopropyl alcohol.

Figures 2A, 2B, 2C:
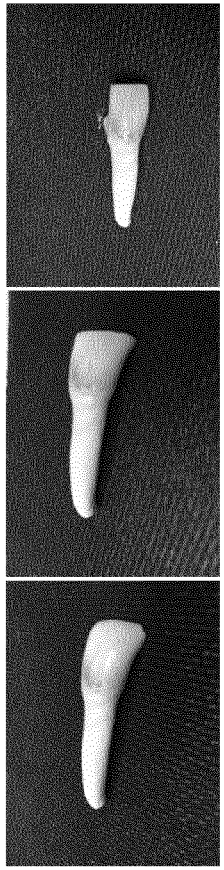
FIGS. 2A-2E are photographs illustrating the tooth preparation and sectioning process.
Figure 2E:
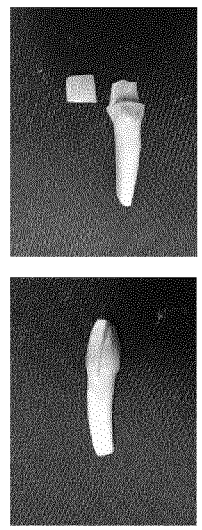
Figure 2D:
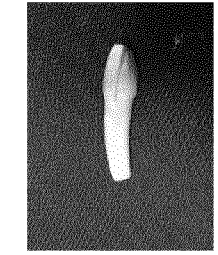

FIG. 2A shows a bovine incisor prior to sectioning. The incisal surface of the tooth was removed with a diamond cutting wheel on a Dremel tool (FIG. 2B). Sectioning was done by first cutting off the proximal surfaces (FIG. 2C) and then the remaining tooth was cut lengthwise from the proximal surface towards the root, keeping parallel to the labial surface of the tooth (FIG. 2D). Lastly, the tooth section was removed by cutting the labial surface such that it meets the lengthwise cut (FIG. 2E).

The tooth section was placed enamel side down in a ¾"×½"×½" Teflon mold. Methacrylate resin (Yates Motloid, Chicago, Ill.) was mixed and poured in the mold containing the tooth section, and cured for 35 minutes. The tooth embedded in resin was removed and then polished on a Unipol-810 Precision Lapping Polishing Machine (MTI Corporation of Richmond, Calif.) with a 2,000 grit diamond wheel at 150 rpm.

Polishing was performed until the dentin tubules were exposed. The polished sections were then placed in a solution of 50 mM lactic acid containing 0.1 wt. % polyacrylic acid for 30 minutes (as described by Karlinsky, et. Al., Journal of Dentistry and Oral Hygiene, Vol. 3 (2) pp. 22-29, February 2011, incorporated herein by reference in its entirety) to remove organic matter, and to demineralize the dentin surface. After the acid wash, the samples were rinsed with deionized water for 20 seconds to remove any residual acid, followed by drying overnight at ambient temperature. After the mounted tooth sections were completely dry, they were labeled and photographed at 100× with an optical microscope (see representative FIG. 3). The mounted teeth sections were placed in a UHMW Delrin holder, and a Byk Gardner Model 5400 Abrasion Tester was used for the brushing studies. The abrasion tester was modified to accept Oral-B toothbrushes.

First, the 3.1 µm spherical silica of Example 2A was evaluated. The toothpaste formulation of Example 2B was diluted for brushing studies at 1:3 in a solution containing 1 wt. % glycerin and 0.1 wt. % Cekol 2000 (C.P. Kelco, Atlanta, Ga.). The toothpaste solution was mixed for 2 minutes with a Silverson model L4RT-A high shear mixer. The brushing machine was turned on and the toothpaste solution was pumped over the tooth sections at a rate of 15 mL/min with a Masterflex peristaltic pump. Brushing ceased after 300 brush strokes, and the tooth sections were rinsed with deionized water for 20 seconds to remove residual toothpaste. After drying at ambient temperature overnight, photographs were taken with an optical microscope at a magnification of 100× (see representative FIG. 4) to determine the impact of brushing with the toothpaste formulation (Example 2B) containing the 3.1 µm spherical silica particles (Example 2A).

Figure 3:
FIG. 3 is an optical microscope photograph of a mounted tooth section.
Figure 4:
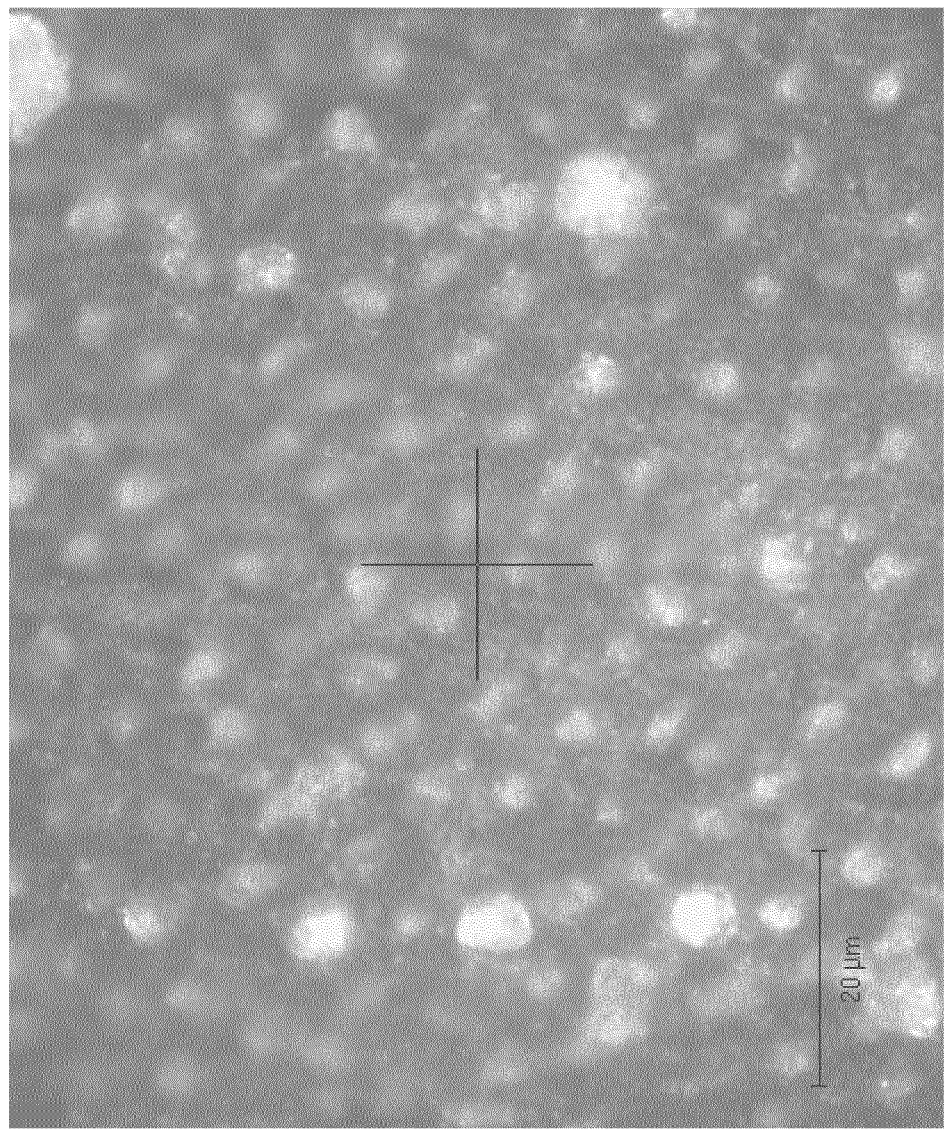
FIG. 4 is an optical microscope photograph of a mounted tooth section after brushing with the toothpaste formulation of Example 2B.
Figure 5:
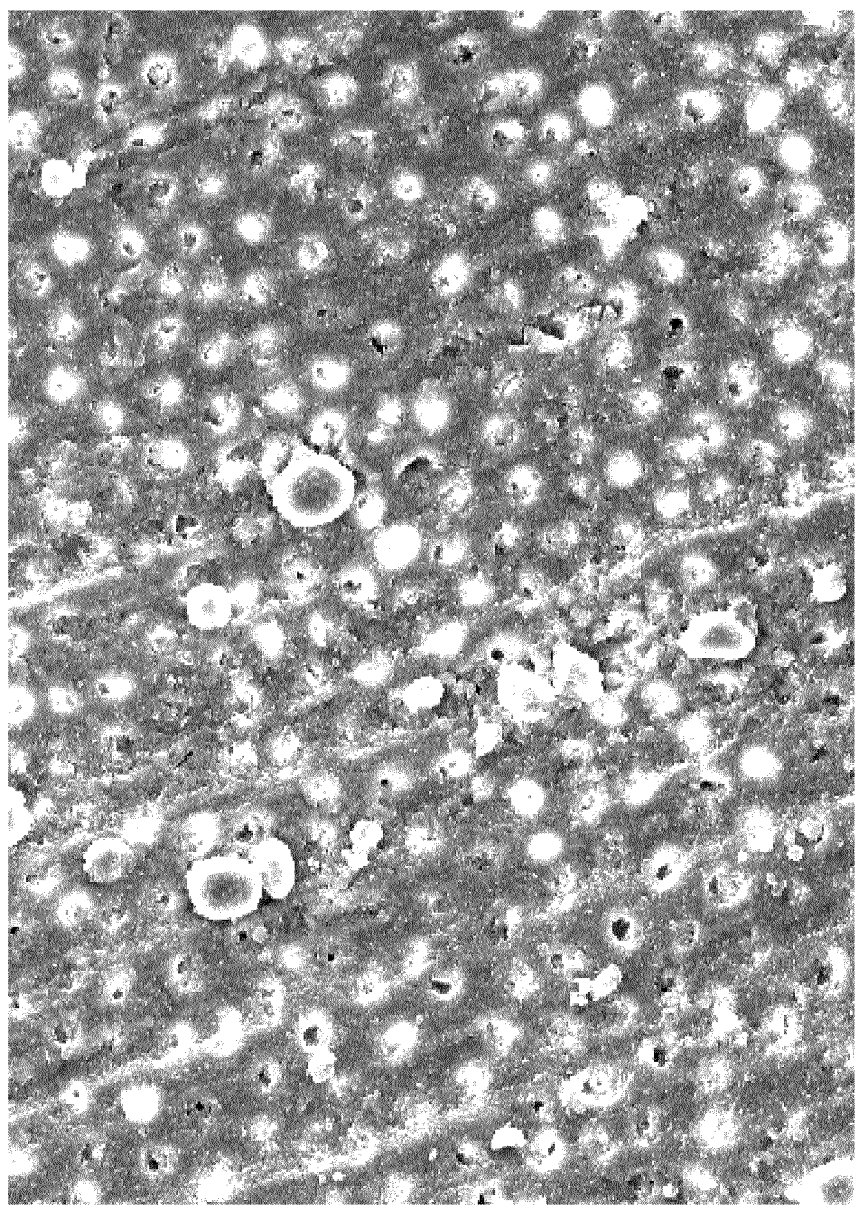
FIG. 5 is a Scanning Electron Micrograph of a mounted tooth section after brushing with the toothpaste formulation of Example 2B.

From FIG. 4, it was unexpectedly found that particles of the 3.1 µm spherical silica resided within the dentin tubules—see the white regions of the image. FIG. 5 is a SEM image of the same tooth dentin as seen in FIGS. 3-4 after brushing with toothpaste formulation 2B, which contained the 3.1 µm spherical silica. In the SEM micrograph of FIG. 5, it was observed, unexpectedly, that the majority of the tubules were occluded with the 3.1 µm spherical silica particles.

Figure 6B:
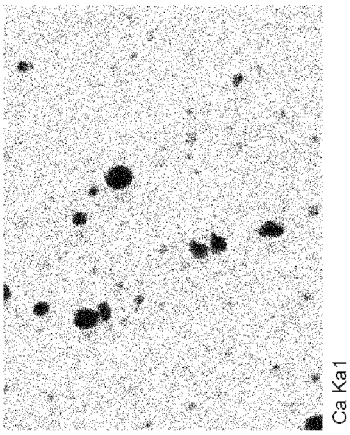
FIGS. 6A-6C are EDS mapping photographs of the dentin surface after brushing with the toothpaste formulations of Example 2B.
Figure 6A:
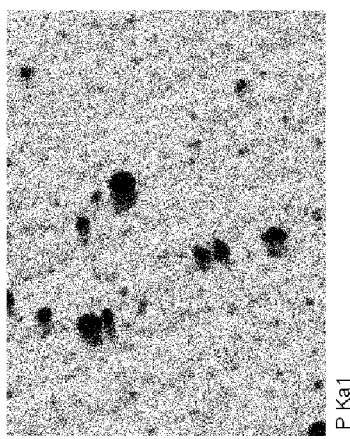
Figure 6C:

FIGS. 6A-6C illustrate the EDS mapping (Electron Dispersive Spectroscopy, Oxford Instruments Inca with Penta FET) of the dentin surface after brushing with toothpaste formulation 2B, which contained the 3.1 µm spherical silica (Example 2A). In FIG. 6A (phosphorous) and FIG. 6B (calcium), the dark spots represent tubules in which phosphorus and calcium, respectively, are not present. In FIG. 6C, the white spots indicate that silicon (from the 3.1 µm spherical silica) now resides in the tubules.

For comparison, toothpaste formulation 1B, which contained the 3.3 µm Example 1A silica—with a non-spherical and irregular particle morphology—was evaluated in the same manner as toothpaste formulation 2B. Example 1A is a fine particle silica product that has been previously shown to occlude dentin tubules in some circumstances.

Figure 7:
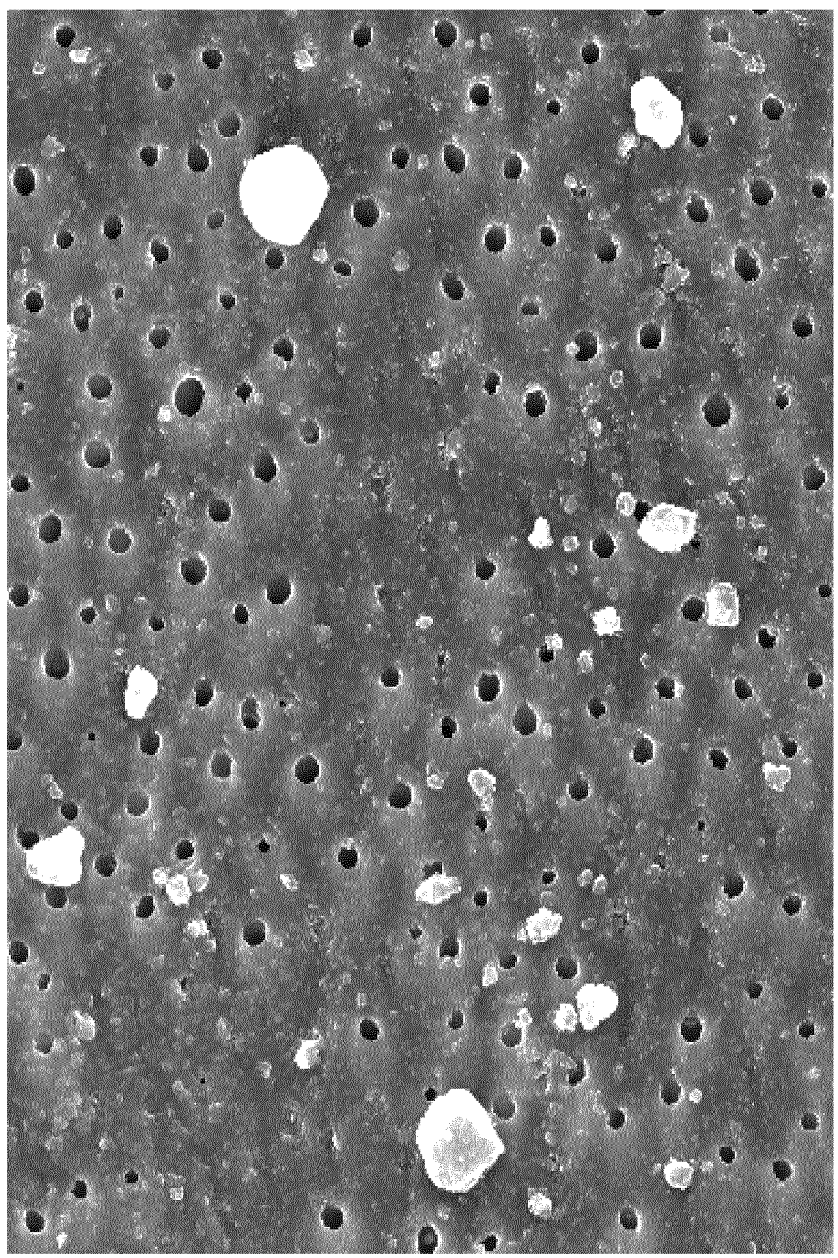
FIG. 7 is a Scanning Electron Micrograph of a mounted tooth section after brushing with the toothpaste formulation of Example 1B.

FIG. 7 is a SEM image of the tooth dentin after brushing with toothpaste formulation 1B, which contained the 3.3 µm non-spherical and irregularly shaped silica. In contrast with the SEM micrograph of FIG. 5, it was observed that the much fewer tubules were occluded with the Example 1A silica particles, despite having approximately the same number of silica particles present in both toothpaste formulations. Clearly, toothpaste formulation 1B resulted in minimal tubule occlusion, and was not as effective as toothpaste formulation 2B.

Figure 8:
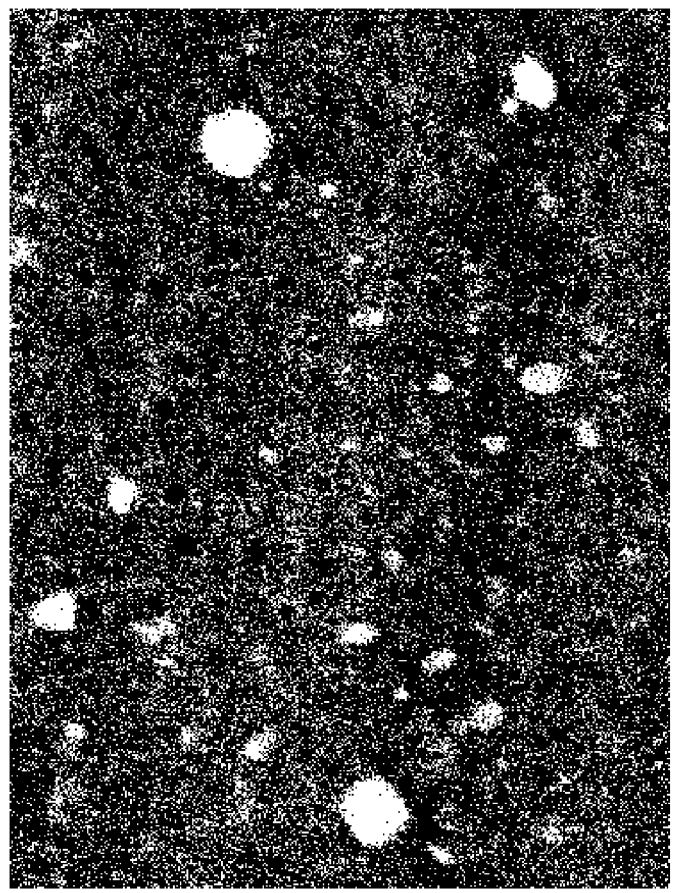
FIG. 8 is an EDS mapping photograph of the dentin surface after brushing with the toothpaste formulation of Example 1B.

EDS mapping in FIG. 8 also demonstrates the less effective tubule occlusion of formulation 1B, where the white spots indicate the presence of silicon (compare with FIG. 6C). Further, the broader particle size distribution of the silica of Example 1A is evident in FIGS. 7-8, in contrast with the narrow particle size distribution of Example 2A.

In summary, the results indicate that toothpaste formulation 2B (containing the 3.1 µm spherical silica particles of Example 2A) was, surprisingly, more likely to occlude dentin tubules after brushing. While not wishing to be bound by theory, it is believed that the small particle size, narrow particle size distribution, and highly spherical particle morphology of the silica particles were significant factors that led to the increase in tubule occlusion. In contrast, toothpaste formulation 1B (containing the 3.3 µm non-spherical and irregularly shaped silica particles of Example 1A) was not nearly as effective at tubule occlusion, likely due to the non-spherical nature (square peg in a round hole analogy) and wider particle size distribution (greater percentage of large particle sizes). Further, the silica of Example 2A can provide superior cleaning performance to that of that of the silica of Example 1A, at least because of the lower oil absorption value and higher pack and pour density properties.

TABLE I

Examples 1A-2A.

| Example | 1A | 2A |
|---|---|---|
| Einlehner (mg lost/100,000 rev) | 0.6 | 3.7 |
| BET Surface Area (m²/g) | 94 | 67 |
| CTAB Surface Area (m²/g) | 79 | 54 |
| Oil Absorption (cc/100 g) | 227 | 68 |
| Water AbC (cc/100 g) | 263 | 82 |
| 5% pH | 7.7 | 7.8 |
| Moisture (%) | 6.9 | 1.33 |
| Median Particle Size (µm) | 3.3 | 3.1 |
| Mean Particle Size (µm) | 3.6 | 3.4 |
| 325 Mesh Residue wt. (%) | <0.1 | <0.1 |

TABLE I-continued

Examples 1A-2A.

| Example | 1A | 2A |
|---|---|---|
| Sodium Sulfate (%) | 0.69 | 0.51 |
| Pour Density (lb/ft³) | 4.9 | 27.5 |
| Pack Density (lb/ft³) | 6.9 | 40 |

TABLE II

Examples 1B-2B - Toothpaste formulations (all values in wt. %).

| | 1B | 2B |
|---|---|---|
| Sorbitol, 70.0% | 64.290 | 60.790 |
| Deionized Water | 13.567 | 12.867 |
| PEG-12 | 3.000 | 3.000 |
| Cekol ® 2000 | 0.400 | 0.400 |
| Sodium Saccharin | 0.200 | 0.200 |
| Sodium Fluoride | 0.243 | 0.243 |
| Thickener | | |
| Zeodent ® 165 | 7.500 | 7.500 |
| Example 2A silica | | 5.000 |
| Example 1A silica Abrasive | 0.800 | |
| Zeodent ® 120 | 10.000 | 10.000 |
| Total | 100.000 | 100.000 |

We claim:

1. Particles, which are silica and/or silicate particles, Wherein the silica and/or silicate particles have:
   (i) a d50 median particle size in a range from about 1 to about 5 µm;
   (ii) a d95 particle size of less than or equal to about 8 µm;
   (iii) an oil absorption in a range from about 40 to about 100 cc/100 g;
   (iv) a pack density in a range from about 20 to about 60 lb/ft³;
   (v) a sphericity factor ($S_{80}$) of greater than or equal to about 0.9;
   (vi) a water absorption (AbC) in a range from about 55 to about 115 cc/100 g; and
   (vii) a BET surface area in a range from about 25 to about 100 m²/g.

2. The particles of claim 1, wherein the d50 median particle size is in a range from about 1.5 to about 4 µm.

3. The particles of claim 1, wherein the d50 median particle size is in a range from about 2 to about 4.5 µm.

4. The particles of claim 1, wherein the d95 particle size is less than or equal to about 7 µm.

5. The particles of claim 1, wherein the d95 particle size is less than or equal to about 6 µm.

6. The particles of claim 1, wherein the oil absorption is in a range from about 50 to about 85 cc/100 g.

7. The particles of claim 1, wherein the oil absorption is in a range from about 60 to about 80 cc/100 g.

8. The particles of claim 1, wherein the pack density is in a range from about 30 to about 50 lb/ft³.

9. The particles of claim 1, wherein the pack density is in a range from about 35 to about 45 lb/ft³.

10. The particles of claim 1, wherein the silica and/or silicate particles have an Einlehner abrasion value in a range from about 1 to about 10 mg lost/100,000 revolutions.

11. The particles of claim 1, wherein the silica and/or silicate particles have an Einlehner abrasion value in a range from about 2 to about 7 mg lost/100,000 revolutions.

12. The particles of claim 1, wherein the silica and/or silicate particles have a BET surface area in a range from about 40 to about 90 m$^2$/g.

13. The particles of claim 1, wherein the silica and/or silicate particles have a water absorption (AbC) in a range from about 70 to about 100 cc/100 g.

14. The particles of claim 1, wherein the silica and/or silicate particles have a 325 mesh residue of less than or equal to about 0.5 wt. %.

15. The particles of claim 1, wherein the silica and/or silicate particles have a 325 mesh residue of less than or equal to about 0.2 wt. %.

16. The particles of claim 1, wherein the sphericity factor ($S_{80}$) is greater than or equal to about 0.92.

17. The particles of claim 1, wherein the sphericity factor ($S_{80}$) is greater than or equal to about 0.94.

18. The particles of claim 1, wherein the silica and/or silicate particles are precipitated silica and/or silicate particles.

19. The particles of claim 1, wherein the silica and/or silicate particles are amorphous.

20. The particles of claim 1, wherein the silica and/or silicate particles comprise precipitated silica particles.

21. The particles of claim 1, wherein the silica and/or silicate particles comprise sodium aluminosilicate particles, sodium magnesium aluminosilicate particles, calcium silicate particles, magnesium silicate particles, or any combination thereof.

22. A composition comprising the particles of claim 1.

23. A dentifrice composition comprising the particles of claim 1.

24. A dentifrice composition comprising from about 0.5 to about 50 wt. % of the particles of claim 1.

25. A dentifrice composition comprising from about 5 to about 35 wt. % of the particles of claim 1.

26. The dentifrice composition of claim 23, wherein the dentifrice composition further comprises at least one of a humectant, a solvent, a binder, a therapeutic agent, a chelating agent, a thickener other than the silica and/or silicate particles, a surfactant, an abrasive other than the silica and/or silicate particles, a sweetening agent, a colorant, a flavoring agent, and a preservative, or any combination thereof.

* * * * *